(12) United States Patent  
Naruse et al.

(10) Patent No.: US 10,588,485 B2  
(45) Date of Patent: Mar. 17, 2020

(54) MEDICAL-SYSTEM CONTROL METHOD

(71) Applicant: OLYMPUS CORPORATION, Tokyo (JP)

(72) Inventors: Masato Naruse, Tokyo (JP); Shintaro Inoue, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 562 days.

(21) Appl. No.: 15/241,629

(22) Filed: Aug. 19, 2016

(65) Prior Publication Data

US 2017/0042406 A1    Feb. 16, 2017

Related U.S. Application Data

(63) Continuation of application No. PCT/JP2015/052151, filed on Jan. 27, 2015.

(30) Foreign Application Priority Data

Feb. 26, 2014    (JP) .................................. 2014-035655

(51) Int. Cl.
*A61B 1/00*    (2006.01)
*A61B 5/06*    (2006.01)
*A61B 1/01*    (2006.01)

(52) U.S. Cl.
CPC ........ *A61B 1/00006* (2013.01); *A61B 1/0008* (2013.01); *A61B 1/00009* (2013.01);
(Continued)

(58) Field of Classification Search
CPC .................................................. A61B 1/0051
(Continued)

(56) References Cited

U.S. PATENT DOCUMENTS 5,269,289 A    12/1993    Takehana et al.
2005/0149003 A1    7/2005    Tierney et al.
(Continued)

FOREIGN PATENT DOCUMENTS

EP    2 052 671 A2    4/2009
EP    2 215 960 A1    8/2010
(Continued)

OTHER PUBLICATIONS

Extended Supplementary European Search Report dated Nov. 13, 2017 in European Patent Application No. 15 75 5552.5.
(Continued)

*Primary Examiner* — Alexandra L Newton
(74) *Attorney, Agent, or Firm* — Scully, Scott, Murphy & Presser, P.C.

(57) ABSTRACT

A medical-system control method including a switching-instruction step in which an instruction for switching between two different control states of the bendable section provided at a distal end of the insertion section is received; an angle-difference calculation step in which the difference between the current angle of the bendable section at the time when the instruction is received and the final target angle of the bendable section in the control state after being switched is calculated; a target calculation step in which, when the calculated difference exceeds a predetermined threshold, a minute angle, smaller than the threshold, is added to the current angle to calculate the target angle, and, when the difference is less than or equal to the threshold, the difference is added to the current angle to calculate the target angle; and a driving step in which the bendable section is driven to the calculated target angle.

9 Claims, 10 Drawing Sheets

(52) U.S. Cl.
CPC ...... *A61B 1/00045* (2013.01); *A61B 1/00098* (2013.01); *A61B 1/00133* (2013.01); *A61B 5/06* (2013.01); *A61B 1/00154* (2013.01); *A61B 1/01* (2013.01)

(58) Field of Classification Search
USPC .................................................. 606/130, 117
See application file for complete search history.

(56) References Cited

U.S. PATENT DOCUMENTS

| | | | |
|---|---|---|---|
| 2005/0272971 A1* | 12/2005 | Ohnishi | A61B 1/00009 600/101 |
| 2007/0265502 A1 | 11/2007 | Minosawa et al. | |
| 2009/0112060 A1* | 4/2009 | Sugiyama | A61B 1/00098 600/104 |
| 2009/0209819 A1 | 8/2009 | Kitagawa et al. | |
| 2010/0204547 A1 | 8/2010 | Tanaka et al. | |
| 2012/0265132 A1* | 10/2012 | Nomura | A61B 1/00098 604/95.04 |

FOREIGN PATENT DOCUMENTS

| | | |
|---|---|---|
| EP | 2 583 616 A1 | 4/2013 |
| JP | H04-129695 A | 4/1992 |
| JP | H04-221527 A | 8/1992 |
| JP | 2007-301378 A | 11/2007 |
| JP | 2008-110071 A | 5/2008 |
| JP | 2009-101077 A | 5/2009 |
| JP | 2013-017785 A | 1/2013 |
| JP | 5153787 B2 | 2/2013 |
| JP | 2014-004310 A | 1/2014 |
| WO | WO 2012/132637 A1 | 10/2012 |

OTHER PUBLICATIONS

International Search Report dated Apr. 21, 2015 issued in PCT/JP2015/052151.
Japanese Office Action dated May 16, 2017 in Japanese Patent Application No. 2014-035655.

* cited by examiner

MEDICAL-SYSTEM CONTROL METHOD

CROSS-REFERENCE TO RELATED APPLICATIONS

This is a continuation of International Application PCT/JP2015/052151 which is hereby incorporated by reference herein in its entirety.

This application is based on Japanese Patent Application No. 2014-035655, the contents of which are incorporated herein by reference.

TECHNICAL FIELD

The present invention relates to a medical-system control method.

BACKGROUND ART

In a known medical system in the related art, an endoscope having a bendable section at a distal end thereof and a treatment tool are inserted into the abdominal cavity through a trocar inserted into the abdomen, and the bendable section of the endoscope is controlled such that the field of view moves in a manner matching the end position, detected by a sensor provided on the trocar, of the treatment tool (for example, see PTL 1).

In the medical system of PTL 1, in a state in which an affected part is being treated and in which the bendable section of the endoscope is controlled so as to quickly follow the end position of the treatment tool, when the distal end of the treatment tool is moved by a large amount to treat another affected part, the bendable section of the endoscope is also bent by a large amount so as to quickly follow the end position of the treatment tool.

CITATION LIST

Patent Literature

{PTL 1} Publication of US Patent Application No. 2005/0149003, Description

SUMMARY OF INVENTION

Solution to Problem

An aspect of the present invention provides a medical-system control method in which, in a medical system having an insertion section of an endoscope inserted into the body through a through-hole in a trocar, two different control states of a bendable section provided at a distal end of the insertion section are switched, the method including: a switching-instruction step in which a switching instruction for switching the control state is received; an angle-difference calculation step in which the angle difference between a current angle of the bendable section when the switching instruction is received in the switching-instruction step and a final target angle of the bendable section in the control state after being switched is calculated; a target calculation step in which, when the angle difference calculated in the angle-difference calculation step exceeds a predetermined threshold, a minute angle, which is smaller than the threshold, is added to the current angle to calculate a target angle, and in which, when the angle difference is less than or equal to the threshold, the angle difference is added to the current angle to calculate the target angle; and a driving step in which the bendable section is driven to the target angle calculated in the target calculation step.

DESCRIPTION OF EMBODIMENTS

A control method, according to a first embodiment of the present invention, for a medical system 1 will be described below with reference to the drawings.

Figure 1:
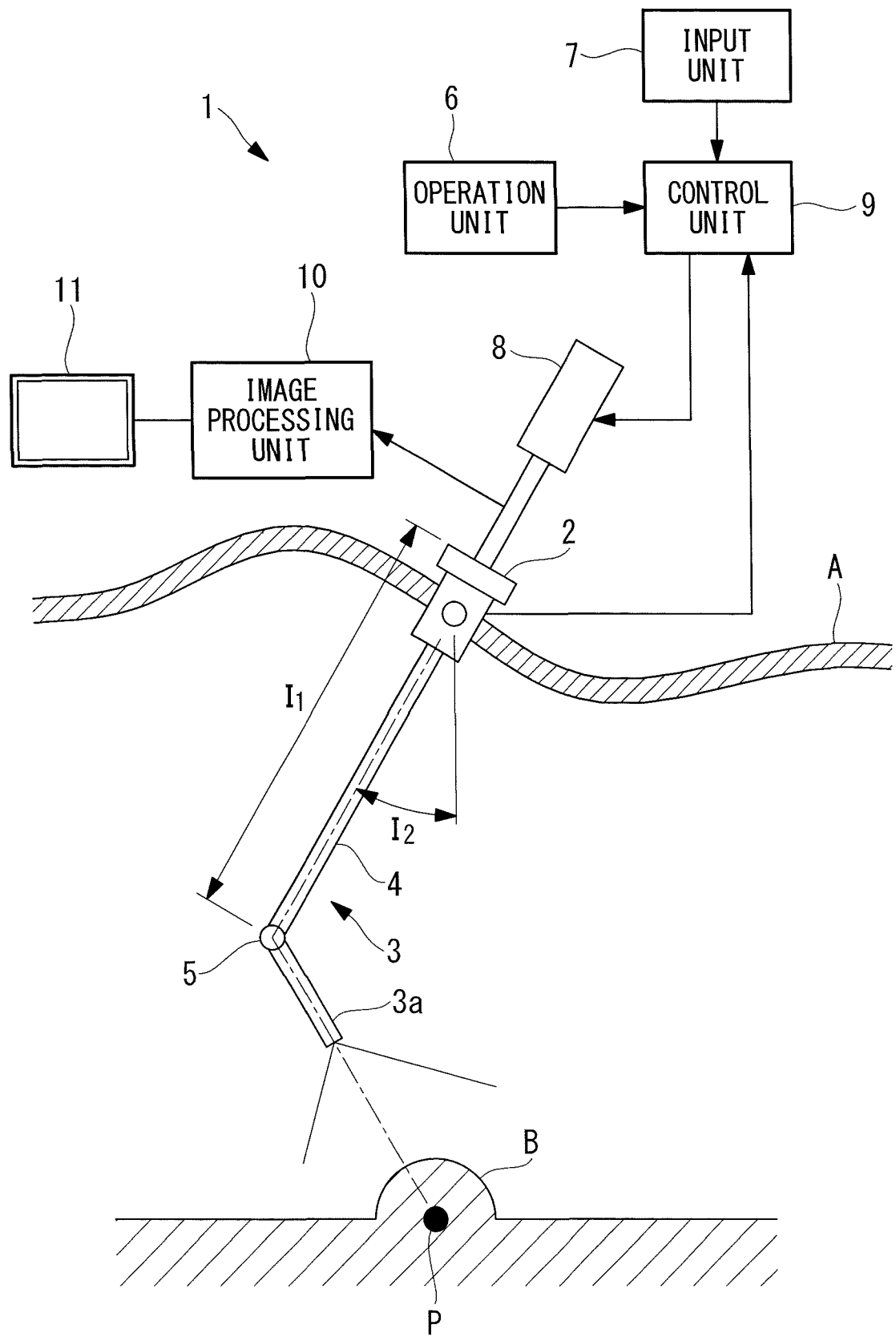
FIG. 1 is a diagram showing the overall configuration of a medical system to which a control method according to a first embodiment of the present invention is applied.

The control method according to this embodiment is applied to the medical system 1 shown in FIG. 1.

As shown in FIG. 1, this medical system 1 includes a trocar 2 disposed through body surface tissue A; a rigid endoscope 3 inserted through the trocar 2; an operation unit 6 for manually instructing the swivel angle of a joint (bendable section) 5 provided at a distal end of an insertion section 4 of the endoscope 3; an input unit 7 that sets the coordinates of a reference point P, serving as the reference for the part to be observed, such as an affected part B, in the body and instructs switching of the control state; a driving unit 8 for driving the joint 5; a control unit 9 for controlling the driving unit 8; an image processing unit 10 for generating an image from a signal acquired by the endoscope 3; and a monitor 11 for displaying the image formed by the image processing unit 10.

The trocar 2 is provided with sensors (not shown) for detecting the insertion amount $I_1$, in the longitudinal axial direction, of the insertion section 4 of the endoscope 3 and the inclination angle $I_2$ of the longitudinal axis with respect to the vertical line.

In this embodiment, the endoscope 3 has a single joint 5. The joint 5 is provided at an end of the rigid insertion section 4 and changes the angle of the longitudinal axis of a distal end section 3a relative to the longitudinal axis of the insertion section 4.

On the basis of the instruction signal from the operation unit 6, the control unit 9 controls the driving unit 8 by using a first control state, in which the driving unit 8 is driven so as to cause the joint 5 to swivel in accordance with the instruction signal, and a second control (cooperative control) state, in which the joint 5 is caused to swivel such that the longitudinal axis of the distal end section 3a passes through the preset reference point P. The control unit 9 also implements a third control state for switching from the first control state to the second control state when receiving, from the input unit 7, a switching instruction for switching from the first control state to the second control state.

Next, the control method, according to this embodiment, for the medical system 1 will be described with reference to FIGS. 2 and 3.

Figure 2:
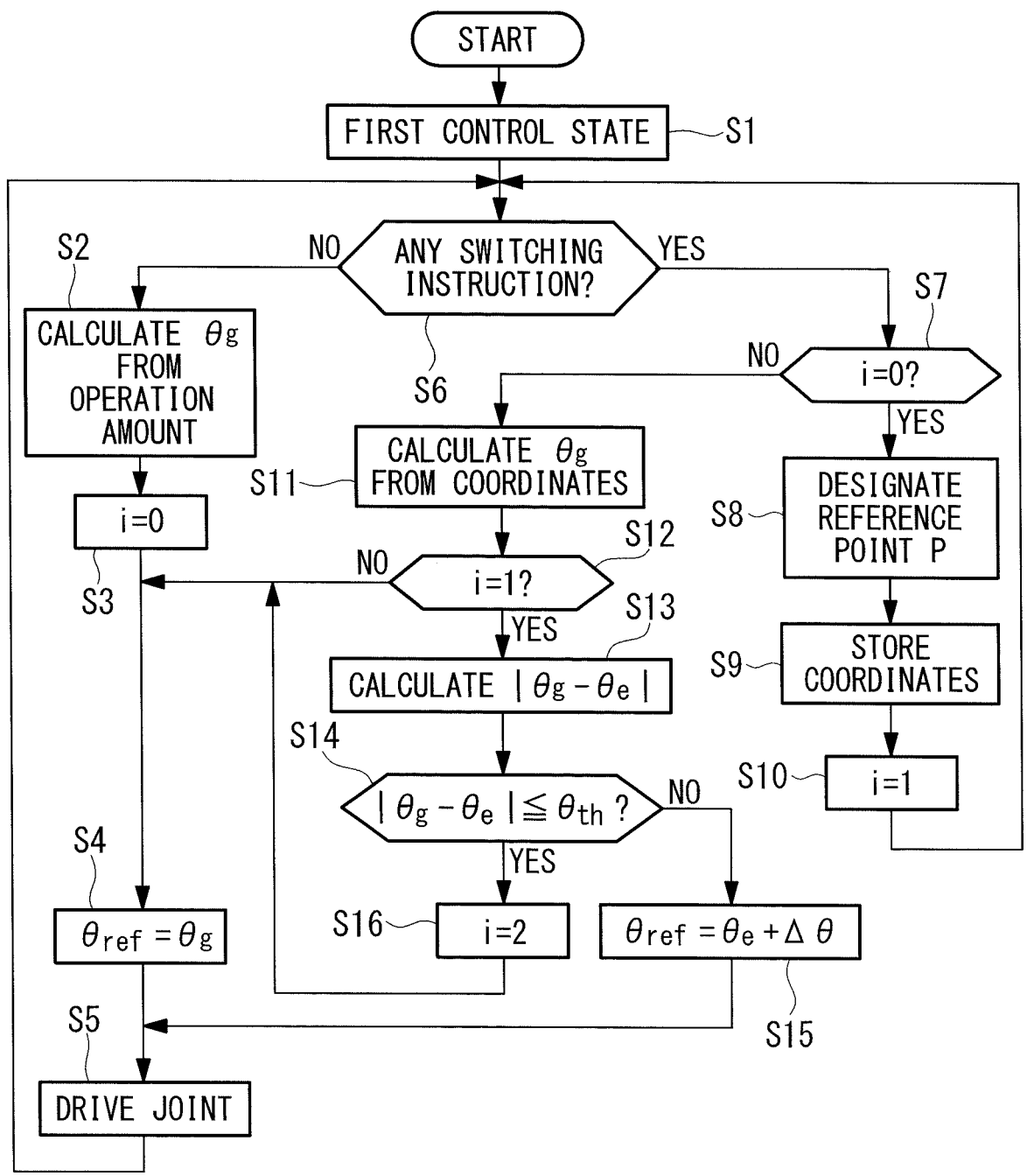
FIG. 2 is a flowchart showing the control method in FIG. 1.
Figure 3:
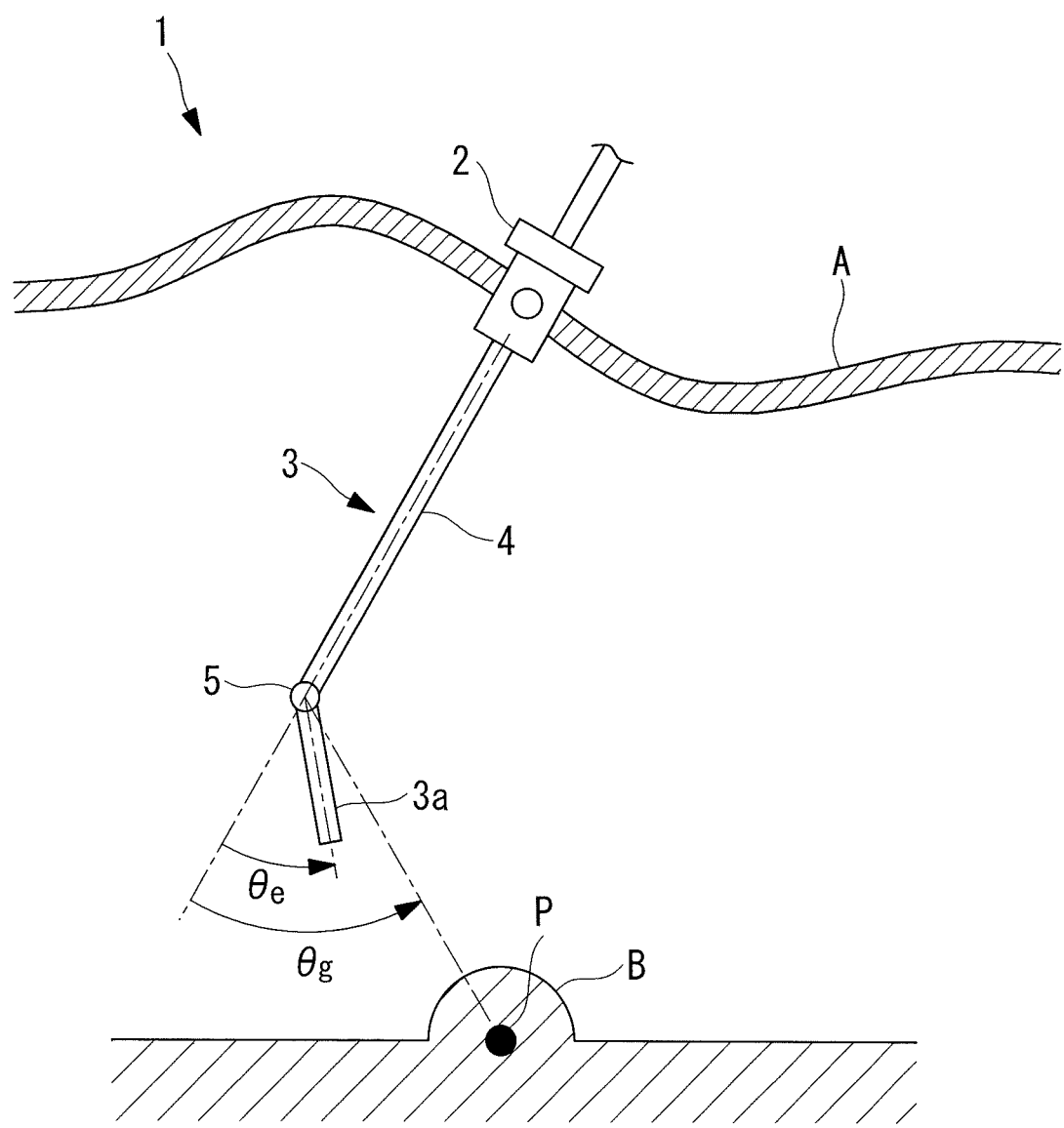
FIG. 3 is a diagram for describing the control method in FIG. 1, showing a distal end section of an endoscope.

As shown in FIG. 2, in the control method according to this embodiment, in a state in which the first control state is selected (step S1), when an operator operates the operation unit 6 while observing the image acquired by the endoscope 3, displayed on the monitor 11, a final target angle $\theta_g$ of the joint 5 corresponding to the operation amount given by manual operation via the operation unit 6 is calculated (step S2), and a flag i is set to zero (step S3). Then, the final target angle $\theta_g$ is set also as a target angle $\theta_{ref}$ of the joint 5 (step S4), and the driving unit 8 is driven such that the joint 5 forms the target angle $\theta_{ref}$ (step S5). Unless a switching instruction is input, the process from step S2 to step S5 is repeated, so that the first control state is maintained.

Next, when the operator inputs a switching instruction for switching to the second control state via the input unit 7 (steps S6 and S7), first, the operator is prompted to designate the coordinates of the reference point P. When the operator designates the reference point P for specifying the affected part B or the like on the image displayed on the monitor 11 (step S8), the coordinate values of the designated reference point P is stored (step S9). Thereafter, the flag is set to 1 (step S10). Note that the coordinates of the reference point P may be stored in advance. In such a case, steps S8 and S9 are omitted.

Then, from the stored coordinate values of the reference point P, the final target angle $\theta_g$ is calculated (step S11). The final target angle $\theta_g$ is calculated in the following manner.

Specifically, because the coordinates of the joint 5 provided at the distal end of the insertion section 4 are calculated from the insertion amount $I_1$ and the inclination angle $I_2$ of the rigid insertion section 4, which are detected by the sensors provided on the trocar 2, the angle formed between a line segment connecting the coordinates of the trocar 2 and the coordinates of the joint 5 (i.e., the longitudinal axis of the insertion section 4) and a line segment connecting the coordinates of the joint 5 and the coordinates of the reference point P (i.e., the longitudinal axis of the distal end section 3a) is calculated as the final target angle $\theta_g$.

This final target angle $\theta_g$ indicates the swivel angle of the joint 5 when the reference point P is located on the optical axis of an image-capturing optical system, provided at a distal end of the distal end section 3a, of the endoscope 3, and the endoscope 3 directly faces the reference point P.

Thereafter, whether or not the switching instruction for switching to the second control state has just been input is determined on the basis of whether or not the flag i is 1 (step S12), and, if the flag i is 1, the third control state is implemented.

In the third control state, first, the difference between the final target angle $\theta_g$ of the joint 5 and a current angle $\theta_e$, $|\theta_g-\theta_e|$, is calculated (step S13), and it is determined whether or not the difference $|\theta_g-\theta_e|$ is less than or equal to a predetermined threshold $\theta_{th}$ (step S14). If, as a result of the determination, the difference $|\theta_g-\theta_e|$ is greater than the threshold $\theta_{th}$, an angle obtained by adding a minute angle $\Delta\theta$, which is smaller than the threshold $\theta_{th}$, to the current angle is set as the target angle $\theta_{ref}$ (step S15), and the process from step S5 is repeated. Herein, for example, a constant that is sufficiently smaller than the threshold $\theta_{th}$ may be set as the minute angle $\Delta\theta$.

If, as a result of the determination, the difference $\Delta\theta$ is less than or equal to the threshold $\theta_{th}$, the flag i is changed to 2 (step S16), and then the process from step S4 is repeated. By doing so, thereafter, the second control state, in which the joint 5 is driven so as to follow the coordinate values of the reference point P, is implemented.

Specifically, with the control method, according to this embodiment, for the medical system 1, when the first control state, in which the joint 5 is driven by the driving unit 8 according to the operation amount given by manual operation, is switched to the second control state, in which the reference point P is set, and the joint 5 is automatically driven by the driving unit 8 so as to follow the reference point P, if the difference between the current angle $\theta_e$ and the final target angle $\theta_g$, $|\theta_g-\theta_e|$, is greater than the predetermined threshold $\theta_{th}$, the control state is not directly switched. Hence, it is possible to prevent a drastic change of the image acquired by the endoscope 3, as in the case where the control state is directly switched.

Before the first control state is switched to the second control state, the third control state, in which the target angle $\theta_{ref}$ shifted from the current angle $\theta_e$ by the minute angle $\Delta\theta$ is set and the joint 5 is bent, is implemented once. Hence, there is an advantage in that it is possible to gradually change the image displayed on the monitor 11, preventing the operator from losing sight of the affected part B or feeling a sense of incongruity.

In this embodiment, although a constant that is sufficiently smaller than the threshold $\theta_{th}$ is set as the minute angle $\Delta\theta$, instead, a value obtained by multiplying the difference between the final target angle $\theta_g$ and the current angle $\theta_e$, $|\theta_g-\theta_e|$, by 1/n (n is an integer greater than 2) may be set as the minute angle $\Delta\theta$. By doing so, it is possible to set the minute angle $\Delta\theta$ that is proportional to the magnitude of the difference $|\theta_g-\theta_e|$ and to drive the joint 5 at a higher speed when the difference $|\theta_g-\theta_e|$ is large and at a lower speed when the difference $|\theta_g-\theta_e|$ is small.

Furthermore, when the insertion amount $I_1$ and the inclination angle $I_2$ of the insertion section 4 are changed by operating the endoscope 3 while the third control state is implemented, a value smaller than the threshold $\theta_{th}$ that is proportional to the amount of movement $\Delta P$ thereof may be set as the minute angle $\Delta\theta$. By doing so, it is possible to drive the joint 5 at a higher speed when the amount of movement $\Delta P$ of the insertion section 4 is large and at a lower speed when the amount of movement $\Delta P$ of the insertion section 4 is small. Herein, the amount of movement $\Delta P$ of the insertion section 4 may be any one of the insertion amount $I_1$, the inclination angle $I_2$, and the magnitude of the vector of their composition.

Specifically, when the insertion section 4 is advanced or retracted (a change in the insertion amount $I_1$) or tilted (a change in the inclination angle $I_2$) during switching from the first control state, in which manual control is performed, to the second control state, in which automatic control is performed, the target angle $\theta_{ref}$ is updated according to the operation. Thus, it is possible to gradually bring the control state toward an ideal state achieved in the second control state and to more naturally switch the control state.

Next, a control method, according to a second embodiment of the present invention, for a medical system 20 will be described below with reference to the drawings.

In the description of this embodiment, the configurations common to those of the control method, according to the above-described first embodiment, for the medical system 1 will be denoted by the same reference signs, and descriptions thereof will be omitted.

Figure 4:
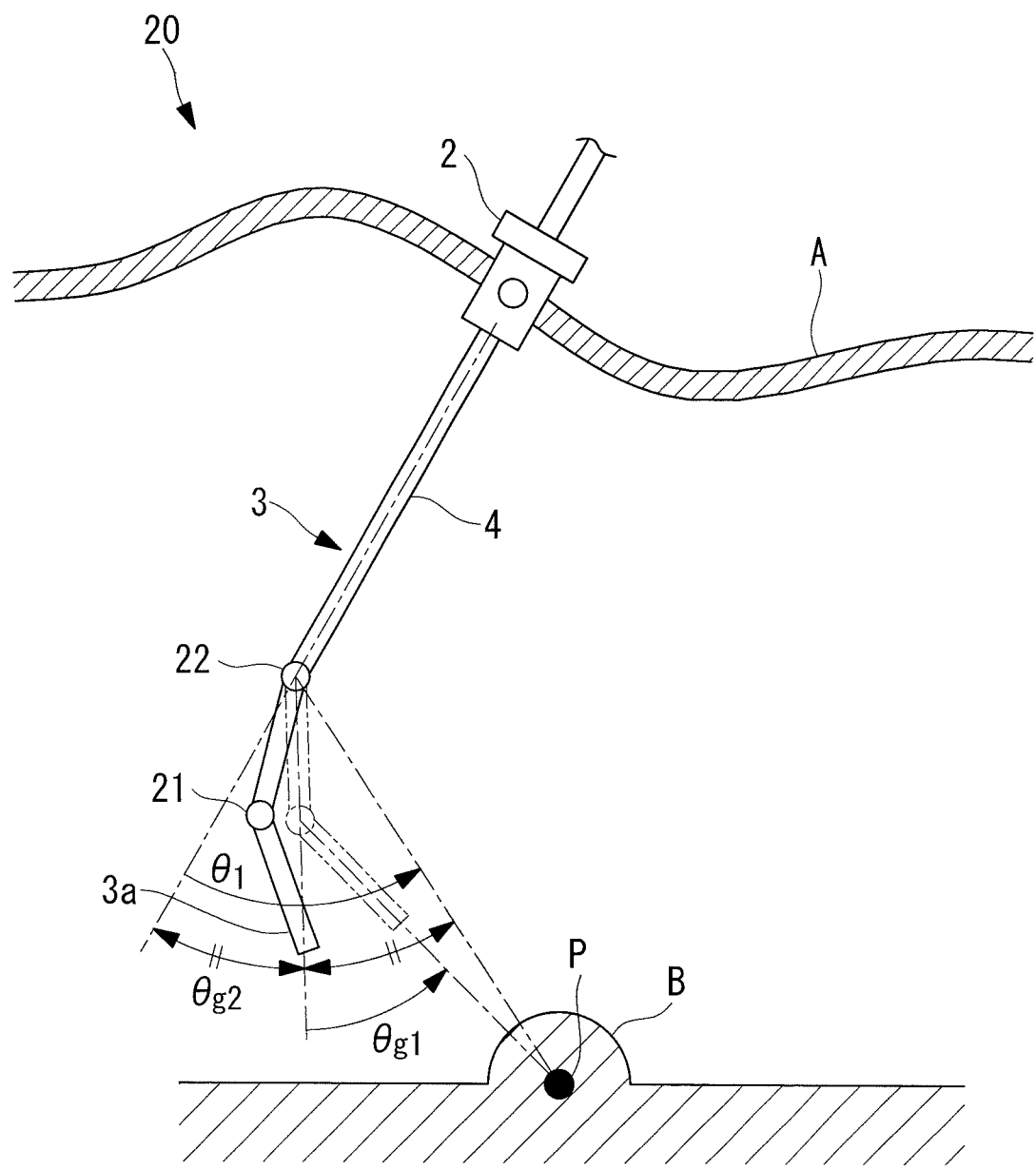
FIG. 4 is a diagram for describing a medical-system control method according to a second embodiment of the present invention, showing a distal end section of an endoscope.

The control method according to this embodiment is applied to the medical system 20, shown in FIG. 4, that includes the endoscope 3 having two joints 21 and 22, which swivel about parallel axes, at the end of the insertion section 4.

Also regarding the movement of these two joints 21 and 22, on the basis of an instruction signal from the operation unit 6, the control unit 9 implements the first control state, in which the driving unit 8 is driven so as to cause the joints 21 and 22 to swivel by an angle corresponding to the operation amount, and the second control state, in which the driving unit 8 is driven so as to cause the joints 21 and 22 to swivel such that the longitudinal axis of the distal end section 3a passes through the preset reference point P.

More specifically, in the second control state, first, a swivel angle $\theta_1$, at which the preset reference point P is located on the longitudinal axis of the distal end section 3a when only the joint 22 on the proximal end side is swiveled with the swivel angle of the joint 21 on the distal end side being set to zero (a state in which the portion between the joint 22 on the proximal end side and the distal end is straight), is obtained, and half of this swivel angle $\theta_1$ is set as a final target angle $\theta_{g2}$ of the joint 22 on the proximal end side. Next, a swivel angle at which the preset reference point P is located on the longitudinal axis of the distal end section 3a when only the joint 21 on the distal end side is swiveled with the joint 22 on the proximal end side being swiveled by the final target angle $\theta_{g2}$ is obtained, and this swivel angle is set as the final target angle $\theta_{g1}$ of the joint 21 on the distal end side. In the second control state, the control unit 9 controls the driving unit 8, which causes the two joints 21 and 22 to swivel, such that these final target angles $\theta_{g1}$ and $\theta_{g2}$ are achieved in the respective sampling periods.

Figure 5:
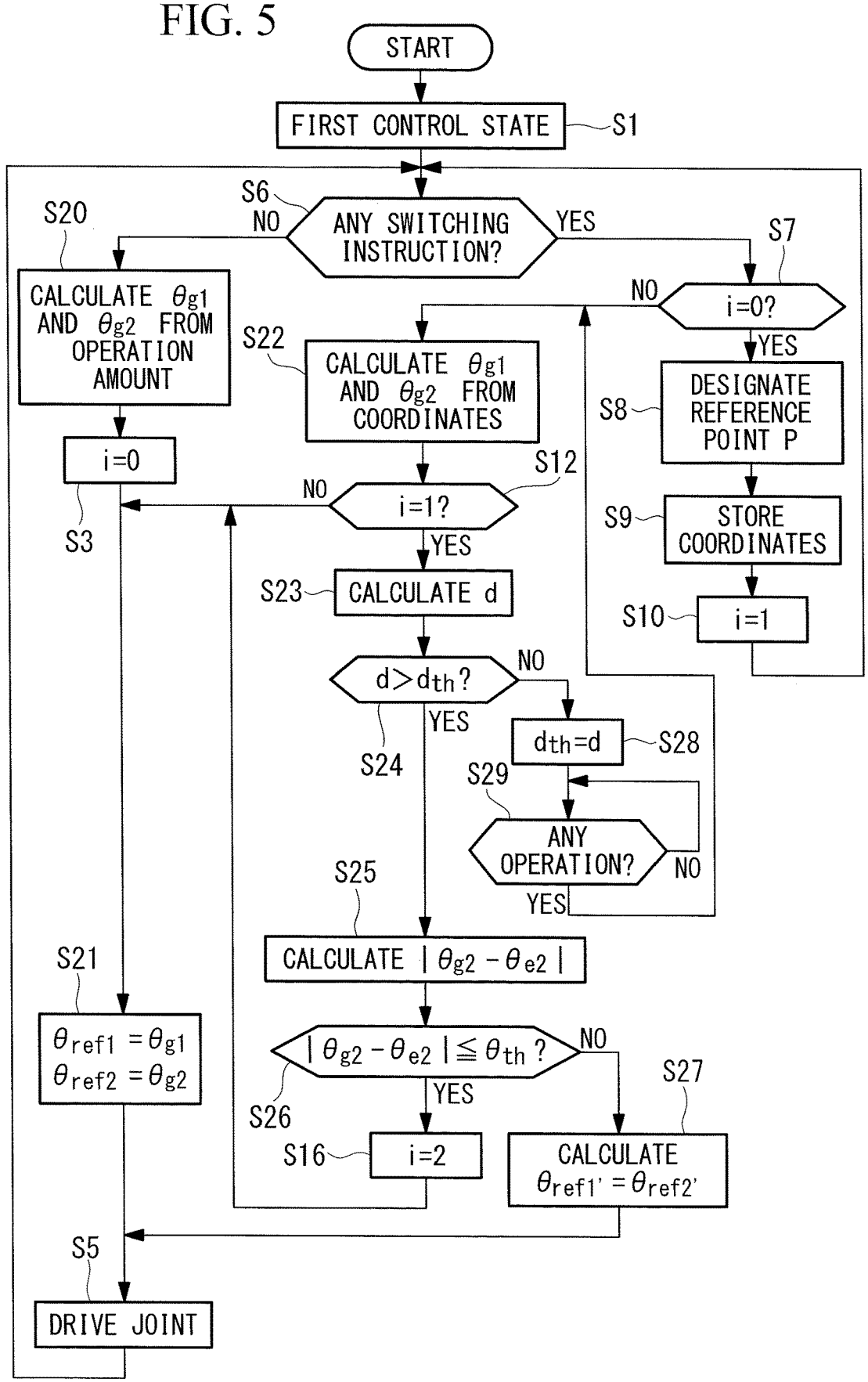
FIG. 5 is a flowchart showing the control method in FIG. 4.

Furthermore, in the control method, according to this embodiment, for the medical system 20, as shown in FIG. 5, in the first control state, the final target angles $\theta_{g1}$ and $\theta_{g2}$ of the joints 21 and 22 corresponding to the operation amount given by manual operation via the operation unit 6 are calculated (step S20), the flag i is set to zero (step S3), the final target angles $\theta_{g1}$ and $\theta_{g2}$ are set also as target angles $\theta_{ref1}$ and $\theta_{ref2}$ of the joints 21 and 22 (step S21), and the driving unit 8 is driven such that the joints 21 and 22 are at the target angles $\theta_{ref1}$ and $\theta_{ref2}$ (step S5).

Next, when the operator inputs a switching instruction for switching from the first control state to the second control state (steps S6 and S7), and the coordinates of the reference point P are designated and stored (step S8 and S9), the final target angles $\theta_{g1}$ and $\theta_{g2}$ are calculated (step S22), and the distance, d, between the distal end of the endoscope 3 and the reference point P when the final target angles $\theta_{g1}$ and $\theta_{g2}$ are achieved is calculated (step S23). Then, it is determined whether or not the calculated distance d is greater than a predetermined threshold $d_{th}$ (step S24).

When the distance d is greater than the threshold $d_{th}$, the difference between the final target angle $\theta_{g2}$ of the joint 22 on the proximal end side and a current angle $\theta_{e2}$, $|\theta_{g2}-\theta_{e2}|$, is calculated (step S25), and it is determined whether or not the difference $|\theta_{g2}-\theta_{e2}|$ is less than or equal to the predetermined threshold $\theta_{th}$ (step S26).

If, as a result of the determination, the difference $|\theta_{g2}-\theta_{e2}|$ is greater than the threshold $\theta_{th}$, an angle obtained by adding a minute angle $\Delta\theta_2$, which is smaller than the threshold $\theta_{th}$, to the current angle $\theta_{e2}$ is set as the target angle $\theta_{ref2}$, the target angle $\theta_{ref1}$ of the joint 21 on the distal end side when the joint 22 on the proximal end side moves by the target angle $\theta_{ref2}$ is calculated (step S27), and the process from step S5 is repeated.

If, as a result of the determination, the difference $|\theta_{g2}-\theta_{e2}|$ is less than or equal to the threshold $\theta_{th}$, the process from step S21 is repeated.

On the other hand, when the calculated distance d is small, the calculated distance d is set to be equal to the threshold $d_{th}$ (step S28). Then, actuation of the joints 21 and 22 is stopped, and the process waits until the changed distance d becomes greater than the new threshold $d_{th}$, as a result of the operator operating the insertion section 4 to change the insertion amount $I_1$ or the inclination angle $I_2$ (step S29). That is, the process from step S22 is repeated. Then, after the operator operates the insertion section 4, new final target angles $\theta_{g1}$ and $\theta_{g2}$ are calculated (step S22), and, when the distance d calculated on the basis of the new final target angles $\theta_{g1}$ and $\theta_{g2}$ is greater than the threshold $d_{th}$, the operation from step S25 is performed.

The thus-configured control method, according to this embodiment, for the medical system 20 has an advantage that, when the first control state, in which manual control is performed, is switched to the second control state, in which automatic control is performed, if the distance d between the distal end and the reference point P when the control state is switched to the second control state is smaller than the threshold $d_{th}$, the switching to the second control state is stopped to prevent the end of the insertion section 3 from getting too close to the affected part B.

Furthermore, as in the first embodiment, when the distance d is greater than the threshold $d_{th}$, the joints 21 and 22 can be driven such that the image displayed on the monitor 11 is gradually changed, which leads to an advantage in that the operator does not lose sight of the affected part B or does not feel a sense of incongruity.

Note that, in this embodiment, although the swivel angle $\theta_1$ at which the preset reference point P is located on the longitudinal axis of the distal end section 3a when only the joint 22 on the proximal end side is swiveled is obtained, and half of this swivel angle $\theta_1$ is set as the final target angle $\theta_{g2}$ of the joint 22 on the proximal end side, the configuration is not limited thereto. The final target angle $\theta_{g2}$ may be calculated by multiplying the swivel angle $\theta_1$ by a set ratio K.

Figure 6B:
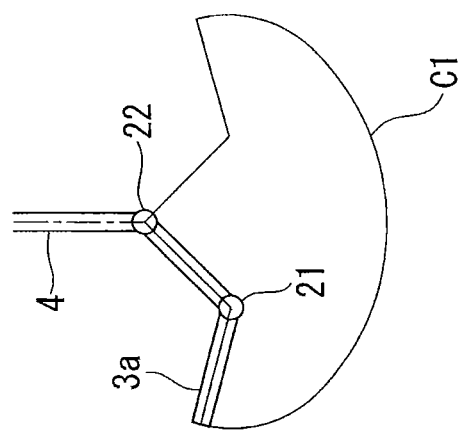
FIG. 6($a$) is a diagram showing a distal end section of an endoscope, and FIG. 6($b$) is a diagram showing a movable range of joints in a first modification of the control method in FIG. 4.
Figure 6A:
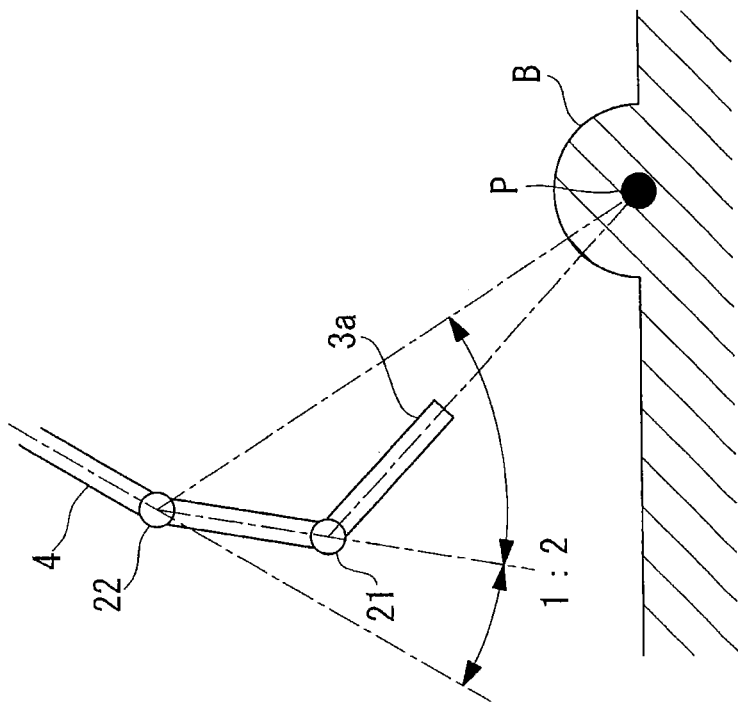

For example, when 1/3 is employed as the ratio K, as shown in FIGS. 6(a) and 6(b), a movable range C1 results, in which the joint 22 on the proximal end side moves by a small amount and the joint 21 on the distal end side moves by a large amount. This is suitable for observation in a small space, in which the distal end can be moved by a large amount, even with a narrow entrance.

Figure 7B:
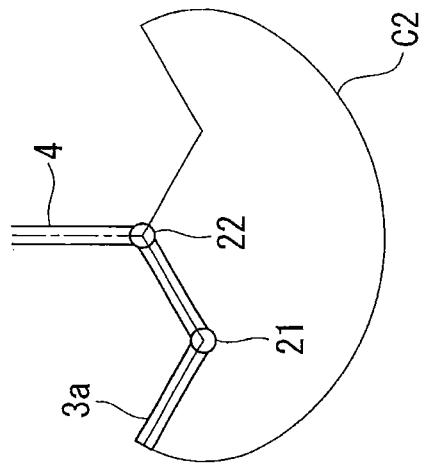
FIG. 7($a$) is a diagram showing a distal end section of an endoscope, and FIG. 7($b$) is a diagram showing a movable range of joints in a second modification of a control method in FIG. 4.
Figure 7A:
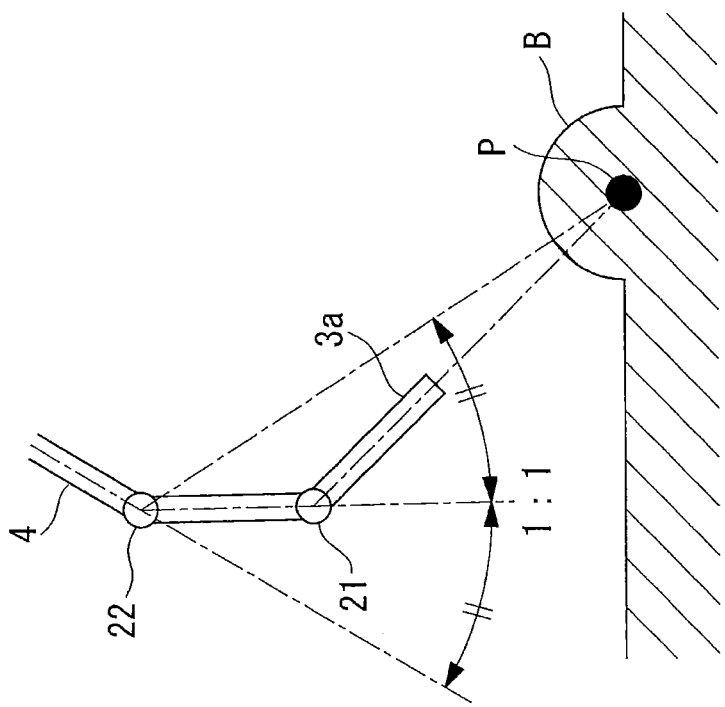

Furthermore, in the above-described method in which 1/2 is employed as the ratio K, as shown in FIGS. 7(a) and 7(b), a movable range C2 results, in which the joint 21 on the distal end side and the joint 22 on the proximal end side are moved by equal amounts. This allows standard observation to be performed.

Figure 8B:
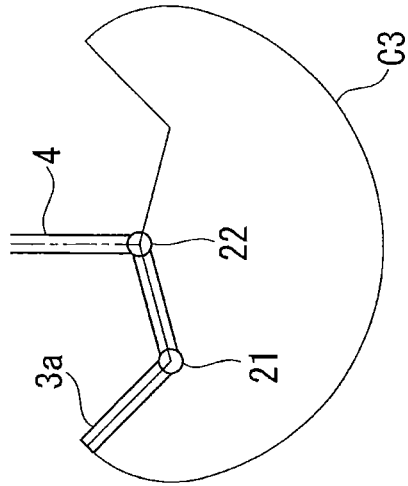
FIG. 8($a$) is a diagram showing a distal end section of an endoscope, and FIG. 8($b$) is a diagram showing a movable range of joints in a third modification of a control method in FIG. 4.
Figure 8A:
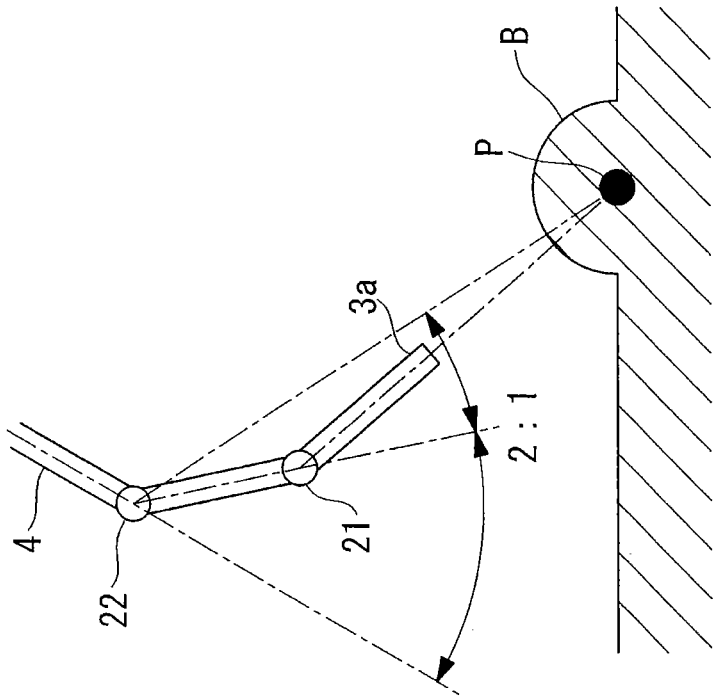

Furthermore, when 2/3 is employed as the ratio K, as shown in FIGS. 8(a) and 8(b), a movable range C3 results, in which the joint 22 on the proximal end side moves by a large amount. Because the joint 22 on the proximal end side moves by a large amount in the wide movable range C3, this is suitable for observing a large space in detail.

A plurality of these ratios K may be registered, and one of them may be selected according to the type of observation.

Next, a control method, according to a third embodiment of the present invention, for a medical system 30 will be described below with reference to the drawings.

In the description of this embodiment, the configurations common to those of the control method, according to the above-described first embodiment, for the medical system 1 will be denoted by the same reference signs, and descriptions thereof will be omitted.

The control method, according to this embodiment, for the medical system 30 differs from that according to the first embodiment in that it is used when a first control state in which automatic control is performed is switched to a second control state in which automatic control is performed, whereas the control method according to the first embodiment is used when the first control state in which manual control is performed is switched to the second control state in which automatic control is performed.

Figure 9:
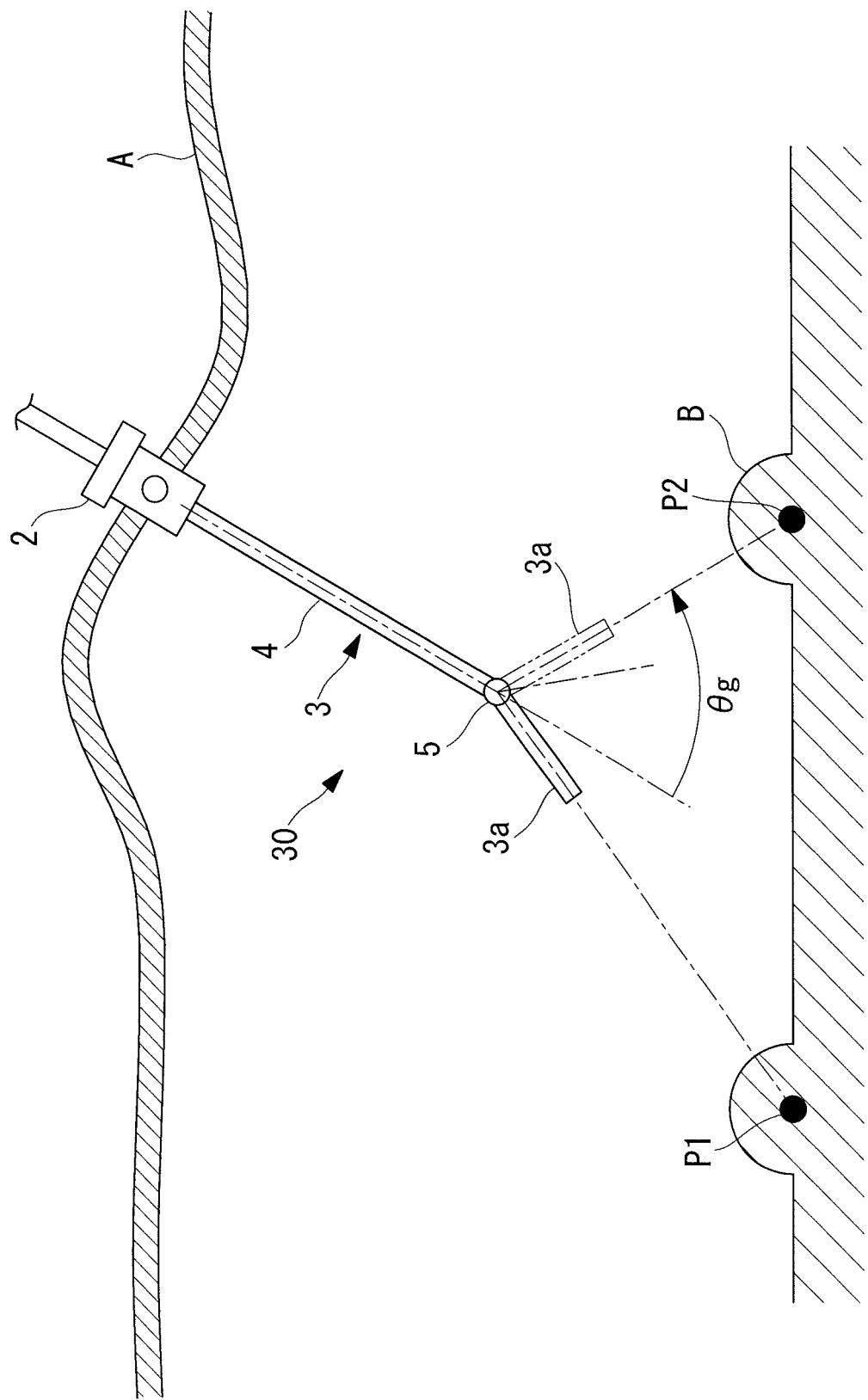
FIG. 9 is a diagram for describing a medical-system control method according to a third embodiment of the present invention, showing a distal end section of an endoscope.

Specifically, in the control method according to this embodiment, as shown in FIG. 9, the coordinates of two or more different reference points P1 and P2 are stored, and a third control state is implemented when the first control state, in which the joint 5 is driven so as to follow one reference point P1 even when the insertion amount $I_1$ or the inclination angle $I_2$ of the insertion section 4 is changed, is switched to the second control state, in which the joint 5 is driven so as to follow another reference point P2.

Figure 10:
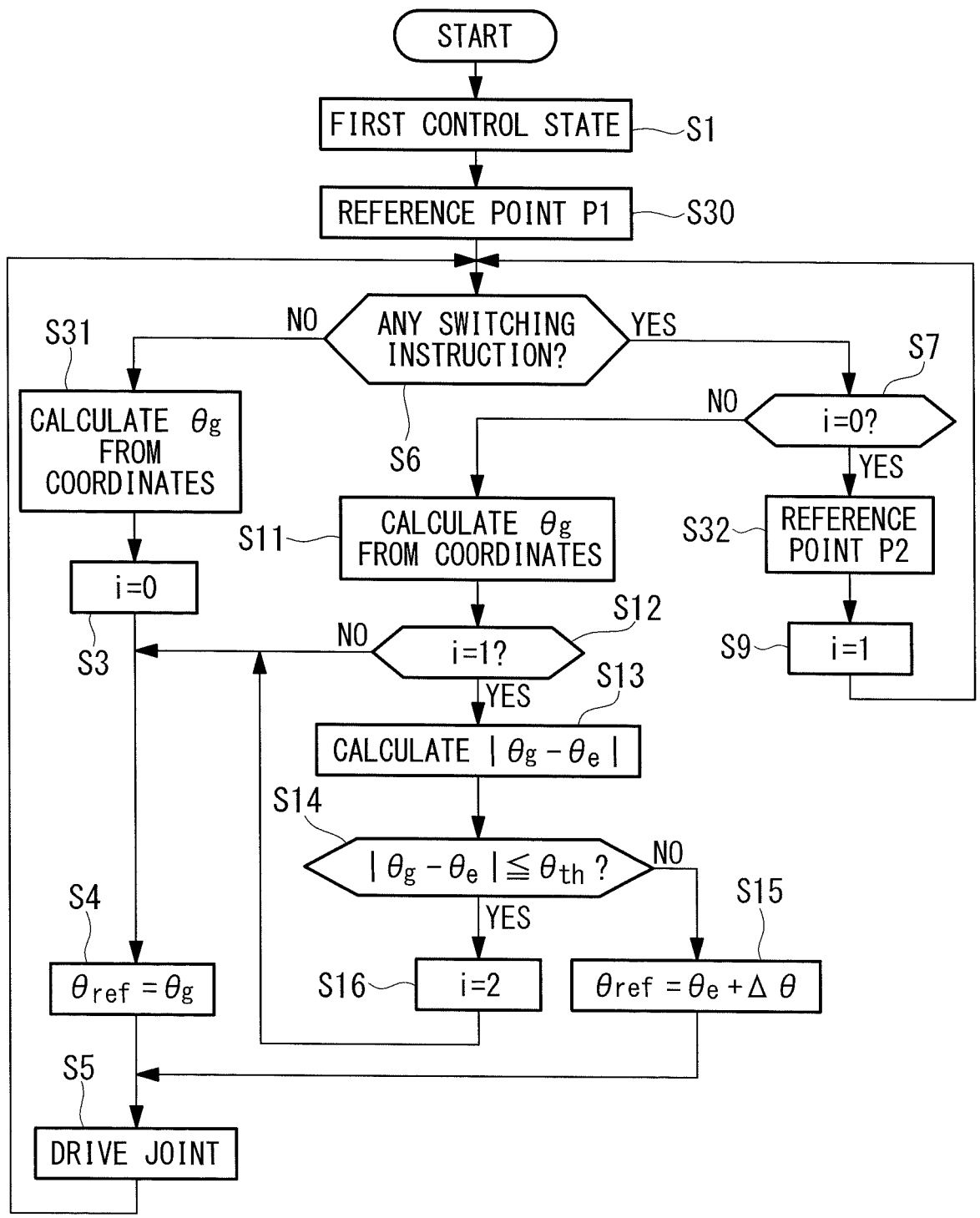
FIG. 10 is a flowchart showing the control method in FIG. 9.

In this case too, as shown in FIG. 10, similarly to the first embodiment, in the first control state (step S1), one reference point P1 is selected (step S30), and the final target angle $\theta_g$ is calculated from the stored coordinate values of the one reference point P1 (step S31). Thereafter, whether or not the switching instruction for switching to the second control state has just been input is determined on the basis of whether or not the flag i is 1 (step S12). If the flag i is 1, the reference point is switched to the reference point P2 (step S32), and the third control state is implemented.

In the third control state, first, the difference between the final target angle $\theta_g$ of the joint 5 and the current angle $\theta_e$, $|\theta_g-\theta_e|$, is calculated (step S13), and it is determined whether or not the difference $|\theta_g-\theta_e|$ is less than or equal to the predetermined threshold $\theta_{th}$ (step S14).

If, as a result of the determination, the difference $|\theta_g-\theta_e|$ is greater than the threshold $\theta_{th}$, an angle obtained by adding a minute angle $\Delta\theta$, which is smaller than the threshold $\theta_{th}$, to the current angle $\theta_e$ is set as the target angle $\theta_{ref}$ (step S15), and the process from step S5 is repeated.

If, as a result of the determination, the difference $|\theta_g-\theta_e|$ is less than or equal to the threshold $\theta_{th}$, after the flag i is changed to 2 (step S16), the final target angle $\theta_g$ is set as the target angle $\theta_{ref}$, and the driving unit 8 is driven to cause the joint 5 to swivel to the final target angle $\theta_g$. In this way, the control state is switched to the second control state.

With the control method according to this embodiment, also when the first control state, in which the joint 5 is controlled so as to follow one reference point P1, is switched to the second control state, in which the joint 5 is controlled so as to follow another reference point P2, an angle moved by a minute angle $\Delta\theta$ from the current angle $\theta_e$ is set as the target angle $\theta_{ref}$ and the joint 5 is swiveled. Thus, there is an advantage that it is possible to gradually change the image displayed on the monitor 11, preventing the operator from losing sight of the affected part B or feeling a sense of incongruity.

The above-described embodiment leads to the following inventions.

An aspect of the present invention provides a medical-system control method in which, in a medical system having an insertion section of an endoscope inserted into the body through a through-hole in a trocar, two different control states of a bendable section provided at a distal end of the insertion section are switched, the method including: a switching-instruction step in which a switching instruction for switching the control state is received; an angle-difference calculation step in which the angle difference between a current angle of the bendable section when the switching instruction is received in the switching-instruction step and a final target angle of the bendable section in the control state after being switched is calculated; a target calculation step in which, when the angle difference calculated in the angle-difference calculation step exceeds a predetermined threshold, a minute angle, which is smaller than the threshold, is added to the current angle to calculate a target angle, and in which, when the angle difference is less than or equal to the threshold, the angle difference is added to the current angle to calculate the target angle; and a driving step in which the bendable section is driven to the target angle calculated in the target calculation step.

According to this aspect, when the distal end of the endoscope with the insertion section thereof being inserted through the through-hole in the trocar is disposed in the body to observe the inside of the body, observation is performed while changing the field of view by moving, relative to the trocar, the insertion section in the longitudinal axial direction, changing the inclination angle of the longitudinal axis, and bending the bendable section at the distal end of the insertion section. In this case, when a switching instruction from one control state to another control state, in which the state of the bendable section is different, is received, the angle difference between the current angle of the bendable section at this time and the final target angle of the bendable section in the control state after being switched is calculated in the angle-difference calculation step. When the angle difference is greater than the threshold, the bendable section is not moved to the final target angle at once, but is driven, in the driving step, to an intermediate target angle. By doing so, it is possible to prevent a drastic change of the field of view of the endoscope. On the other hand, when the angle difference is less than or equal to the threshold, the drastic change of the field of view does not occur, so, it is possible to quickly switch between the different control states by moving the bendable section to the final target angle at once.

In the above-described aspect, the minute angle may be an angle obtained by multiplying the angle difference by 1/n (n is an integer greater than 2).

With this configuration, the minute angle to be added to the current position may be set to a value proportional to the angle difference. Hence, the minute angle may be increased with an increase in the angle difference, making it possible to increase the moving speed.

Furthermore, in the above-described aspect, the medical-system control method may further include: a detection step in which the inclination angle of a longitudinal axis of the insertion section through the trocar and the insertion amount thereof in the longitudinal axial direction are detected; and a final-target-angle calculation step in which the final target angle is calculated on the basis of the coordinate values of a specific reference point in the control state after being switched, the insertion amount, and the inclination angle.

With this configuration, even during the control based on the temporarily-set final target angle, when the insertion amount or the inclination angle of the insertion section with respect to the trocar changes, the final target angle is updated in the final-target-angle calculation step on the basis of the insertion amount or the inclination angle detected in the detection step. Hence, it is possible to gradually bring the bendable section toward the second control state, in response to the operation.

Furthermore, in the above-described aspect, the control state before being switched may be either a control state in which the bendable section is bent according to a manual instruction or a control state in which the bendable section is bent on the basis of the coordinate values of another reference point, the insertion amount, and the inclination angle.

Furthermore, in the above-described aspect, the distance between a distal end of the bendable section and the reference point in the control state after being switched may be calculated after the switching-instruction step, and, when the distance is smaller than a distance threshold, control may be performed such that the distal end of the bendable section is not moved.

Furthermore, in the above-described aspect, the insertion section may include a plurality of bendable sections, a plurality of ratios of the bending amounts of the bendable sections may be stored, and the ratios of the bending amounts may be changed before and after switching the control state.

REFERENCE SIGNS LIST d distance
$d_{th}$ distance threshold
$I_1$ insertion amount
$I_2$ inclination angle
P, P1, P2 reference point
$\theta_e$, $\theta_{e2}$ current angle
$\theta_g$, $\theta_{g1}$, $\theta_{g2}$ final target angle
$\theta_{ref}$, $\theta_{ref1}$, $\theta_{ref2}$ target angle
$\theta_{th}$ threshold
$\Delta\theta$ minute angle
S2, S20 final-target-angle calculation step
S5 driving step
S6 switching-instruction step
S13 angle-difference calculation step
S15 target calculation step
S29 detection step
1, 20, 30 medical system
2 trocar
3 endoscope
4 insertion section
5, 21, 22 joint (bendable section)

The invention claimed is:

1. A method for controlling a first joint of an insertion section of an endoscope, the method comprising:
   interatively performing a process of:
      calculating a final target angle of the first joint;
      calculating an angle difference between a current angle of the first joint and the final target angle of the first joint;
      determining whether the angle difference exceeds a predetermined threshold;
      in response to determining that the angle difference exceeds the predetermined threshold, setting a sum of an angle smaller than a predetermined threshold and the current angle as a reference target angle;
      in response to determining that the angle difference does not exceed the predetermined threshold, setting the final target angle as the reference target angle; and
      driving the first joint to bend to the reference target angle, until the first joint is bent to the final target angle.

2. The method according to claim 1,
wherein the angle smaller than the predetermined threshold is an angle obtained by multiplying the angle difference by 1/n (n is an integer greater than 2).

3. The method according to claim 1, comprising:
detecting an inclination angle of the insertion section through a trocar in a longitudinal axial direction and an insertion amount of the insertion section though the trocar along the longitudinal axial direction; and
calculating the final target angle of the first joint on the basis of the coordinate values of a specific reference point, the insertion amount, and the inclination angle.

4. The method according to claim 3, comprising:
in a first control state, driving the first joint to bend according to a manual instruction; and
in a second control state, iteratively performing the process to drive the first joint to bend to the reference target angle.

5. The method according to claim 3, comprising:
in a first control state:
   calculating the final target angle of the first joint on the basis of the coordinate values of another reference point, the insertion amount, and the inclination angle; and
   driving the first joint to bend to the final target angle; and
in a second control state, iteratively performing the process to drive the first joint to bend to the reference target angle.

6. The method according to claim 4, comprising:
calculating a distance between a distal end of the insertion section that is moved by the bending of the first joint and the specific reference point;
determining whether the distance is smaller than a distance threshold;
in response to determining that the distance is smaller than the distance threshold, performing control such that the distal end of the insertion section is not moved; and
in response to determining that the distance is not smaller than the distance threshold, iteratively performing to process to drive the first joint to bend to the reference target angle.

7. The method according to claim 1,
wherein the insertion section comprises the first joint and a second joint, and
wherein the method further comprises calculating the final target angle of the first joint and a final target angle of the second joint based on one of a plurality of preset ratios of the first target angle and the second target angle.

8. The method according to claim 1, comprising:
in the process that is iteratively performed:
   setting a moving speed of the first joint in accordance with a magnitude of the angle difference; and
   driving the first joint to bend to the reference target angle at the moving speed of the first joint set.

9. The method according to claim 8, comprising:
in the process that is iteratively performed:
   setting the moving speed of the first joint such that the moving speed becomes higher as the magnitude of the angle difference becomes larger.

\* \* \* \* \*